United States Patent
Bergersen

(10) Patent No.: US 11,571,327 B2
(45) Date of Patent: Feb. 7, 2023

(54) WIRE AND RAMPS IN SLEEP HABIT CORRECTOR

(71) Applicant: ORTHO-TAIN, INC., Toa Alta, PR (US)

(72) Inventor: Earl O. Bergersen, Glenview, IL (US)

(73) Assignee: Ortho-Tain, Inc., Toa Alta, PR (US)

( * ) Notice: Subject to any disclaimer, the term of this patent is extended or adjusted under 35 U.S.C. 154(b) by 0 days.

(21) Appl. No.: 17/361,713

(22) Filed: Jun. 29, 2021

(65) Prior Publication Data

US 2022/0409424 A1   Dec. 29, 2022

(51) Int. Cl.
*A61F 5/56*   (2006.01)

(52) U.S. Cl.
CPC .................... *A61F 5/566* (2013.01)

(58) Field of Classification Search
CPC .. A61C 7/08; A61C 7/00; A61C 19/00; A61C 19/06–08; A61F 5/56–58; A63B 71/085; A63B 2071/086; A63B 2071/088; A63B 71/08–085

See application file for complete search history.

(56) References Cited

U.S. PATENT DOCUMENTS

| | | | |
|---|---|---|---|
| 3,871,370 A * | 3/1975 | McDonald | A61C 7/08 128/860 |
| 4,784,605 A | 11/1988 | Bergersen | |
| 4,799,884 A | 1/1989 | Bergersen | |
| 5,092,346 A * | 3/1992 | Hays | A61F 5/566 128/859 |
| 5,645,420 A | 7/1997 | Bergersen | |
| 5,876,199 A | 3/1999 | Bergersen | |
| 6,676,664 B1 | 1/2004 | Al-Assir | |
| 6,870,566 B1 | 3/2005 | Koide | |

(Continued)

FOREIGN PATENT DOCUMENTS

EP   3804655 A1   4/2021

OTHER PUBLICATIONS

International Searching Authority; International Search Report and Written Opinion of the International Searching Authority for PCT/US2021/039577; dated Oct. 26, 2021; pp. 1-11.

*Primary Examiner* — Michelle J Lee
(74) *Attorney, Agent, or Firm* — Taft Stettinius & Hollister LLP; Joseph M. Bennett-Paris

(57) ABSTRACT

A habit corrector appliance including a front portion, a first ramp and a second ramp extending from the front portion. The first ramp is located at a high position adjacent to or at a user's palate to ensure the tongue is positioned at the palate which widens the palate and which also prevents or reduces mouth breathing. The second ramp is located at a position lower than and beneath the first ramp, wherein the second ramp substantially prevents the tongue from entering a lower space within the oral cavity, wherein the first ramp aids in an elevated tongue position and the patient learns to swallow with the tongue elevated to substantially reduce or prevent air from entering the oral cavity through the mouth and to prevent mouth breathing. Slits at the ramp sides allow for lateral expansion of the appliance. Lingual tabs promote proper anterior positioning of the jaws. A lingual wire with narrower anterior wire extensions can provide a widening of the arch and movement of the upper incisors and maxilla in a forward position.

9 Claims, 5 Drawing Sheets

(56) References Cited

U.S. PATENT DOCUMENTS

| | | |
|---|---|---|
| 7,458,810 B2 | 12/2008 | Bergersen |
| 7,963,765 B2 | 6/2011 | Bergersen |
| 8,133,050 B2 | 3/2012 | Bergersen |
| 9,393,083 B2 | 7/2016 | Bergersen |
| 9,517,113 B2 | 12/2016 | Bergersen |
| 10,537,407 B2 | 1/2020 | Bergersen |
| 10,874,593 B2 | 12/2020 | Bergersen |
| 10,980,615 B2 | 4/2021 | Bergersen |
| 11,129,746 B2 * | 9/2021 | Alvarez .................. A61F 5/566 |
| 2005/0037311 A1 | 2/2005 | Bergersen |
| 2007/0240724 A1 | 10/2007 | Bergersen |
| 2012/0225402 A1 * | 9/2012 | Crivello .................. A61C 5/90 523/105 |
| 2017/0071701 A1 | 3/2017 | Bergersen |
| 2018/0256388 A1 | 9/2018 | Magistro |
| 2020/0215384 A1 * | 7/2020 | Farrell ................. A63B 71/085 |
| 2021/0100723 A1 | 4/2021 | Bergersen |

* cited by examiner

Sleep Disordered Breathing Questionnaire

0 – Not Present    1 - 2 Mild      3 - Moderate     4 – 5 Pronounced

Initial Follow Up                        Initial Follow Up

1. _____ _____ Snore at all?

2. _____ _____ Snore only infrequently (1 night/week)

3. _____ _____ Snore fairly often (2-4 nights/week)

4. _____ _____ Snore habitually (5-7 nights/week)

5. _____ _____ Have labored, difficult, loud breathing at night

6. _____ _____ Have interrupted snoring where breathing stops for 4 or more seconds 7. _____ _____ Have stoppage of breathing more than 2 times in an hour 8. _____ _____ Hyperactive 9. _____ _____ Mouth breathes during day 10. _____ _____ Mouth breathes while sleeping 11. _____ _____ Frequent headaches in morning 12. _____ _____ Allergic symptoms 13. _____ _____ Excessive sweating while asleep 14. _____ _____ Talks in sleep 15. _____ _____ Poor ability in school 16. _____ _____ Falls asleep watching TV 17. _____ _____ Wakes up at night 18. _____ _____ Attention deficit 19. _____ _____ Restless sleep 20. _____ _____ Grinds teeth 21. _____ _____ Frequent throat infections 22. _____ _____ Feels sleepy and/or irritable during the day 23. _____ _____ Have a hard time listening and often interrupts 24. _____ _____ Fidgets with hands or does not sit quietly 25. _____ _____ Ever wets the bed 26. _____ _____ Bluish color at night or during the day 27. _____ _____ Speech Problems*
*If yes, provide parent speech questionnaire

Sleep Questionnaire
To be filled out only if #27 was indicated above

Initial Follow Up                        Initial Follow Up

28. _____ _____ Is it difficult to understand your child's speech

29. _____ _____ Difficult to understand over the phone

30. _____ _____ Nasal Speech

31. _____ _____ Speech sounds abnormal

32. _____ _____ Others have difficulty understanding speech

33. _____ _____ Gets frustrated when people can't understand speech

34. _____ _____ Sometimes omits consonants

35. _____ _____ Uses M, N, NG instead of P, F, V, S, Z sounds

36. _____ _____ Hoarseness

37. _____ _____ Lisp

38. _____ _____ Any speech therapy? How long? _____

FIG. 12

WIRE AND RAMPS IN SLEEP HABIT CORRECTOR

TECHNICAL FIELD

The present invention relates to an oral appliance for both children and adults. More specifically, the present invention relates to one or more oral appliances which are used to address abnormal sleep issues in children and adults.

BACKGROUND OF THE DISCLOSURE

The statements in this section merely provide background information related to the present disclosure and should not be construed as constituting prior art.

Habits such as thumb or finger sucking, poor resting position of the tongue, abnormal swallowing, and tongue thrust influence sleep issues that can seriously affect the health of a patient. For example, a poor resting tongue positioned within the body of the mandible forces a child to develop a narrow posterior maxillary arch. This in turn does not encourage the nose to develop volume and can reduce the amount of air passing through the nasal area. Mouth breathing becomes a common way for these individuals or users to breathe.

Thumb or finger sucking also displaces the tongue from being positioned correctly within the palatal area. A child typically swallows twice a minute during daytime and once every minute while sleeping. This represents about 1920 swallows every 16 hours during the day and 480 swallows while asleep or 2400 swallows per day. A mouth breathing habit can easily be developed with this type of abnormal practice. Mouth breathing is strongly associated with the brain functions, immune system and growth changes (not only in the face but in the body as well). These patterns influence the body to have more frequent infections (swollen tonsils and adenoid tissue) further intensifying the problem.

Mouth breathing also allows the mandible and tongue to be posteriorly displaced at night which tends to narrow the oropharynx by about 6 millimeters (mm) for a ½ inch opening of the mouth while sleeping. This produces less oxygen for the child which has a serious effect on the brain, immune and endocrine systems. This explains why a child with sleep disordered breathing can suffer from neurocognitive, behavioral, and social problems.

A need, therefore, exists for an oral appliance that encourages a child or an adult to address abnormal sleep issues to thereby improve the health of the child or adult.

The present invention is intended to improve upon and resolve some of these known deficiencies of the art.

SUMMARY OF THE DISCLOSURE

The habit corrector appliance substantially prevents, corrects, or improves the following issues and provides the following advantages.

Prevents the mandible and tongue from drifting posteriorly during sleep eliminating obstruction of the oropharynx.

Repositions the tongue to position itself into the palate and from being within the body of the mandible.

Substantially prevents mouth breathing and forces the patient to breathe through the nose.

Reduces or corrects thumb sucking.

Reduces or corrects anterior open bite.

Advances the mandible to obtain a correct antero-posterior relation with the maxilla.

Stimulates mandibular condylar growth in retrognathic mandibles (small mandibles).

Reduces or corrects an abnormal bite.

Reduces or prevents tongue thrust.

The appliance includes a handle to pull the appliance in a forward direction, if desired, to strengthen the orbicularis oris muscle. (around the lips).

Widens the posterior arch.

These and other features of the habit corrector appliance are shown and identified in the attached figures of the appliance.

In one embodiment, there is provided a habit corrector appliance including a first ramp and a second ramp. The first ramp extends from a front portion of the appliance, wherein the first ramp is an upper ramp and is located at a high position adjacent to or at a user's palate to direct the tongue to be positioned at the palate, which as a result widens the palate and which also prevents or reduces mouth breathing, since the location of the inferior part of the tongue prevents day mouth breathing. The second ramp extends from the front portion of the appliance, wherein the second ramp is a lower ramp located at a position lower than and beneath the first ramp to substantially prevents the tongue from entering a lower portion of a space within the oral cavity. The first ramp aids in an elevated tongue position and the patient learns to swallow with the tongue elevated to substantially reduce or prevent air from entering the oral cavity through the mouth.

In another embodiment, there is provided a habit corrector appliance including an inner wall spaced from an outer wall, and one or more lower lingual tabs extending from the inner wall. The one or more lingual tabs are configured to reduce a tendency of a lower jaw from slipping rearward while a user sleeps and to increase mandibular advancement and to encourage lower jaw growth.

In a further embodiment, there is provided a method of using a habit corrector appliance having an upper trough and a lower trough. The method relining the upper trough and the lower trough with a self-curing acrylic or similar material to secure the appliance to the mouth and substantially prevent mouth breathing from becoming a habit.

In a further embodiment, there is provided a method of providing to a patient a habit corrector appliance, the habit corrector appliance having an upper trough, with an upper inner shield, and a lower trough, with a lower inner shield. The method includes: adjusting a wire structure located in the upper inner shield to alter the shape of the upper trough, wherein the wire structure includes a curved portion located between ends that are relatively straight; and placing the appliance having the altered shape in the patient's mouth to expand a dental arch of the patient located in the upper trough by moving anterior extensions toward the upper trough to advance the upper incisors and maxilla.

In one or more embodiments, slits are located at the lateral portion of both ramps at the posterior margins to allow for easier expansion of the upper posterior arch.

In an additional embodiment, there is an embedded wire (a diameter of 0.030 inches to 0.045 inches) present around the arch on the lingual side from the front to the rear of the appliance.

An embedded wire may have undulations or curves vertically in the posterior (rear) area to better expand the dental arch in the upper or lower arch.

Three front wire extensions of 0.015" to 0.028" are extended upward from the front main wire to advance the front teeth and maxilla in a forward direction. Other numbers of front wire extensions are contemplated.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein:

FIG. 12 illustrates a questionnaire to determine or diagnose sleep disordered breathing.

Figure 1:
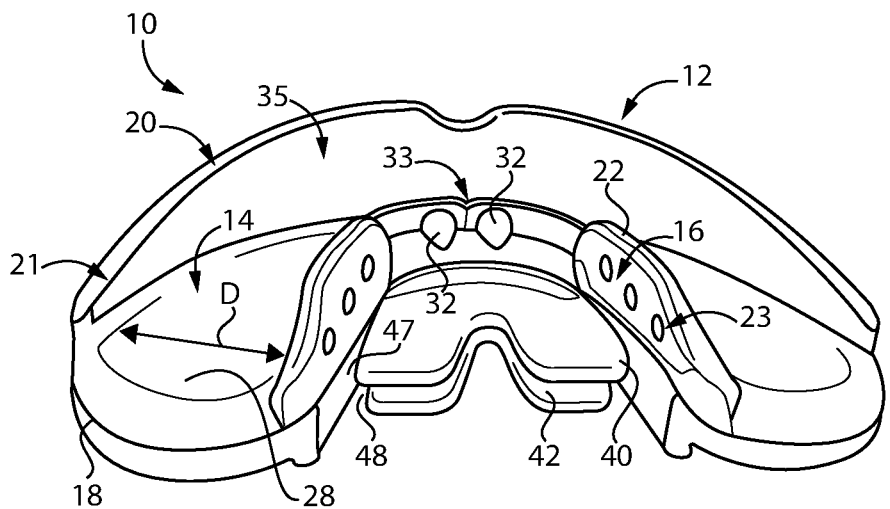
FIG. 1 is a perspective top view of a habit corrector appliance.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

While exemplary embodiments incorporating the principles of the present disclosure have been disclosed herein, the present disclosure is not limited to the disclosed embodiments. Instead, this application is intended to cover any variations, uses, or adaptations of the disclosure using its general principles. Further, this application is intended to cover such departures from the present disclosure as come within known or customary practice in the art to which this invention pertains.

The disclosed habit corrector appliance is used mostly passively at night for individuals that have abnormal sleep issues. The attached figures provide an understanding of the various design features. The disclosed appliance is worn mostly passively at night while sleeping in order to force the patient or individual to breathe through the nose and reduce or stop nighttime mouth breathing. The habit corrector appliance addresses abnormal sleep issues in children (and adults) as well as those habits and growth factors that can be known to influence abnormal sleep issues. FIG. 1 shows both the upper and lower ramps, wherein the upper ramp guides the tongue as far up into the palate as possible, while the lower ramp prevents the tongue from assuming a resting posture within the mandibular body.

FIG. 1 illustrates a habit corrector appliance 10 including a high upper outer shield 12, also identified as a labial shield, to substantially prevent a patient from getting air through the oral cavity when opening the mouth. The habit corrector comes in different sizes to fit different sizes of mouths and engages both the upper teeth and the lower teeth. The high upper outer shield 12 extends upwardly from a trough 14 that is configured to fit the upper teeth, such that the upper teeth are bordered by the outer shield 12, the trough 14, and an inner shield 16. At a rear upper portion 18 of the appliance 10, a lateral distance D between the outer shield 12 and the inner shield 16 is increased to provide a wider trough particularly toward the lingual sides of the tongue. A top edge 20 of the outer shield 12 is higher than a top edge 22 of the inner shield. 16 defined with response to a surface of the trough 14. The top edge 22 of the inner shield 16, while lower than the top edge 20 of the outer shield 12, extends from the trough 14 to provide a high lingual margin for maintaining the sides of the tongue in a position between opposed top edges of the inner shield. The top edge 22 at the location of posterior bumps 23 is higher than a top edge of a wall 32 from which one or more spurs 32 extend.

As used herein "front" means the portion of the appliance configured to be located at the front teeth. The appliance extends from the front teeth toward the rear teeth and defines a central longitudinal axis extending from the front to the back along a center line.

Figure 3:
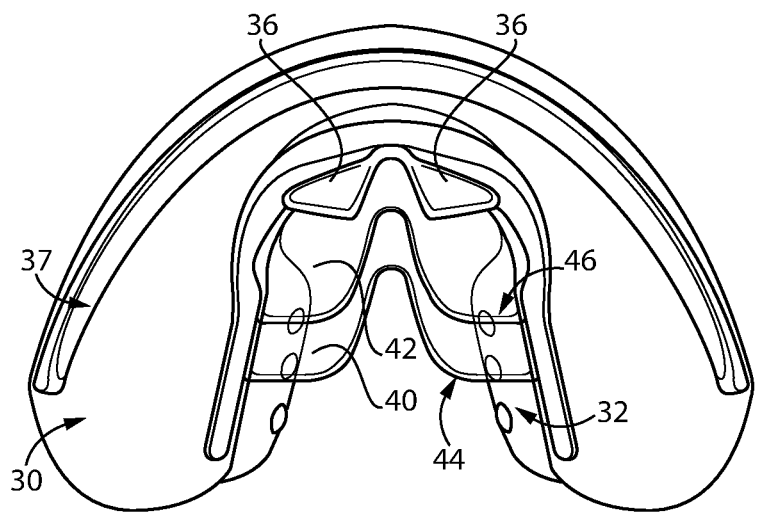
FIG. 3 is a bottom view of a habit corrector appliance.

FIG. 1 further shows a posterior portion of the trough 14 which includes an upper posterior trough 28 and a lower posterior trough 30 as seen in FIG. 3. The upper trough 28 is configured to receive teeth of the upper jaw and the lower trough 30 is configured to receive teeth of the lower jaw. In one embodiment, the lower posterior trough 30 is lined with a self-curing acrylic resin which substantially prevents the jaws from separating while sleeping, particularly at night. The upper posterior trough 28 also includes, in one or more embodiments, a self-curing acrylic resin located in the trough 14. Materials other than a self-curing acrylic resin are contemplated, including heat softening overlays. Additional materials include but are not limited to methyl methacrylate, ethyl methacylate, ethylene vinyl acetate (EVA), or thermal plastic elastomer (TPE). Using the self-curing acrylic resin, the jaws are held together with a closed occlusion to reduce or prevent impingement of the tongue on the oropharynx. This double relining of upper and lower halves (the upper and lower troughs) of the appliance aids in keeping jaws from opening which would then allow mouth breathing. With the relining of both upper and lower halves of appliance mouth breathing is substantially prevented from taking place and becoming a habit. In one or more embodiments, the resin is relatively hard and is not usually replaced with a new resin. If a relining is needed the user may do so. The upper trough 14 and lower trough 30, and shields 12 and 16 are textured to increase the adherences of the liner, even at the interior trough if necessary.

One or more spurs 32 extend from a wall 33 of the inner shield 16 toward the rear of the appliance to substantially prevent the tongue from thrusting forward, reducing the likelihood of tongue thrusting, and encouraging a proper swallow. In other embodiments, a raised area extends from the sidewall of the inner shield in place of or in addition to the spurs 32. The spurs 32 extend in the lingual portion of the upper arch.

FIG. 1 also illustrates the high posterior lingual margins defined by the top edge 22 of the inner shield 16 that enters the lingual soft tissue of the sides of the hard palate and also allows the liner to enter the interproximal areas to increase the retention of the appliance and to prevent mouth opening. In another embodiment shown in FIGS. 4 and 5, a likelihood of dislodgement of the appliance 10 is reduced in which the appliance 10 includes an arch wire 34 molded with the appliance. In one embodiment, the arch wire 34 is a heavy single wire. In other embodiments, multiple wires are molded with the appliance.

Figure 6:
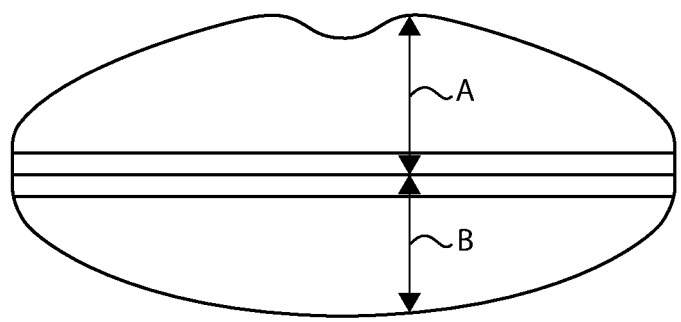
FIG. 6 is a schematic rear view of a habit corrector.

The outer shield 12 includes upper labial shield 35 and lower labial shield 37 (see FIGS. 1, 3, 4, and 6) each of which are higher toward the front of the appliance 10 to reduce or prevent mouth breathing and to encourage nasal breathing. The labial shield 35, having a height A in FIG. 6, and the labial shield 37, having a height B in FIG. 6, are as high as can be tolerated by patients of different ages such as from 1 to 2 years, 3-5 years, 6-8 years, 9-12 years, 13 years and up throughout adulthood. These labial upper and lower shields have to be as high as can be compatible to fit into the oral cavity of these various ages. This is important, since if the patient opens their mouth to get air into the oral cavity and oropharynx the tongue will impinge on the anterior wall of the oropharynx and collapse it and reduce the air (oxygen) flow into the lungs. These shields also prevent and replace mouth breathing with normal nasal breathing.

The following Table 1 illustrates a range of heights for height A and height B for different age groups. The illustrated range of heights, however are exemplary, and heights A and B should not be limited to these specifics heights. Different heights, depending on the patient, are adjusted by reducing the heights or increasing the heights in each age group by a distance of about 5 mm in either direction.

TABLE 1

| Age | A | B |
| --- | --- | --- |
| 2-4 years of age | 11.5 mm | 11.5 mm |
| 4-6 years of age | 13.0 mm | 13.0 mm |
| 6-12 years of age | 20.0 mm | 14.0 mm |
| Adult | 25.0 mm | 15.0 mm |

The front margin 20 of the outer shield 12 is considerably higher, in different embodiments, than the posterior lingual margins 22 of the inner shield 16. The posterior buccal margin 21 (a portion of the top edge 20) is about the same height as the posterior lingual margins 22. These posterior lingual margins 22 are for a different purpose than the front upper shield 35 and front lower shield 37, which are instead for the purpose of preventing mouth breathing and thumb sucking. The posterior margins 21 and 22 are to secure the reline into the interproximals of the canines and posterior teeth to prevent dislodgement of the appliance 10 and to keep the jaws tightly together to prevent the jaws from opening which would enable unwanted mouth breathing.

A reline is the addition of a separate harder plastic, such as a methyl methacrylate or and ethyl methacrylate which are self-cure acrylics, to flow into the embrasures of the teeth, most often the posterior upper and/or lower teeth. The purpose is to secure the appliance to the teeth and prevent it from falling out of the mouth or to keep the mouth from opening when the upper and lower are re-lined with these materials. In some instances, the acrylic can be replaced, but not often, by a dental professional.

The following Table 2 illustrates a range of heights for front margin 20 and posterior lingual margins 22. The illustrated range of height, however, are exemplary, and as such the heights should not be limited to the heights of Table 2. For example, element number 22 is 1.4 times higher than element number 20 at 2-4 years of age, while it is 2.6 times higher at the adult heights. While these heights are exemplary and are generally acceptable for a large number of patients, these distances, in different embodiments, may vary significantly from the heights of Table 2. The third column of Table 2 illustrates a ratio of the heights for element 20 when compared to element 22.

TABLE 2

| #22 | #20 (A) | #20 (A)/#22 |
| --- | --- | --- |
| Age 2-4  8 mm | 11.5 mm | 1.4 |
| Age 4-6  8 mm | 13.0 mm | 1.6 |
| Age 6-12  8 mm | 20.0 mm | 2.5 |
| Adult 9.5 mm | 25.0 mm | 2.6 |

Figure 2:
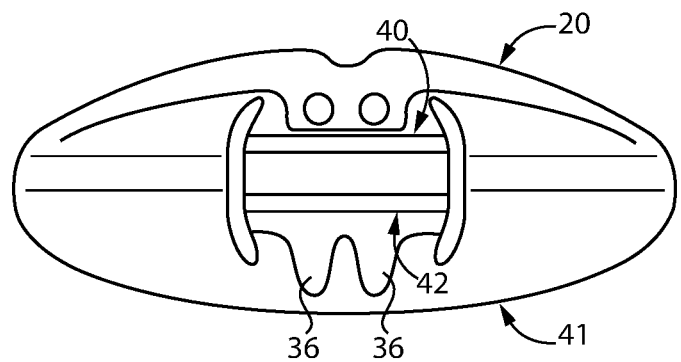
FIG. 2 is a rear view of a habit corrector appliance.

As seen in FIGS. 2 and 3, the appliance 10 includes one or more lower lingual tabs 36 that extend from a lower edge of the inner shield 16. In FIG. 3, the lower lingual tabs 36 extend longitudinally toward the rear of and downwardly from the front portion of the trough 14 to encourage the mandible to be positioned anteriorly (forward) and to prevent the mandible from slipping rearward and the tongue from drifting posteriorly during sleep to increase the treatment success of mouth breathing and mandibular advancement and pressure against the anterior wall of oropharynx which keeps the airway from being restricted which can reduce the oxygen to the body. The lingual tabs 36 are located below the lower ramp or shelf 42 and maintain an open oropharynx. In one or more embodiments, these tabs 36 are from 6 to 10 mm long, approximately 3 to 7 mm longer than the tabs of currently known habit correctors to ensure maximum mandibular advancement, opening of the oropharynx, and to improve correction of nighttime mouth breathing.

The upper posterior lingual tabs or spurs 32 (See FIG. 4) include small projections to remind the child where the tongue belongs when swallowing. The other posterior bumps 23 of FIG. 1 (illustrated as circles) are to indicate where to locate the tongue and to therefore expand the tongue which widens the palate. The posterior bumps 23 remind the user of proper position of the tongue when swallowing. The bumps 23 are located on the lingual surface of the lingual palatal tabs 22. In one or more embodiments, there are usually three (3) of them located on the lingual surface of the palatal tab. Other number of bumps 23 are contemplated. The spurs 32 are also identified as maxillary protrusions that reduce tongue thrust.

As seen in FIGS. 1 and 3, the appliance 10 includes a first ramp or shelf 40 and a second ramp or shelf 42 extending toward the rear of the appliance. The first ramp 40 is larger than the second ramp 42 and includes a terminating edge 44 that extends further towards the rear of the appliance than does a terminating edge 46 of the second ramp 42. Also seen in FIG. 1, the first ramp 40 is elevated with respect to the second ramp 42 and consequently is closer to the palate than the second ramp 42 is to the palate. The upper, larger, longer first ramp 40 elevates the tongue into the palate and the lower, smaller, and shorter second ramp 42 substantially prevents and discourages the tongue from positioning itself into the mandibular body. There is a space between the bottom of the first ramp 40 and the top of the second ramp 42 enough to reduce the likelihood of, or to prevent, the tongue from entering anywhere below or to be positioned below the first ramp 40. In another embodiment, there could be a connection between the two ramps 40 and 42.

Figure 4:
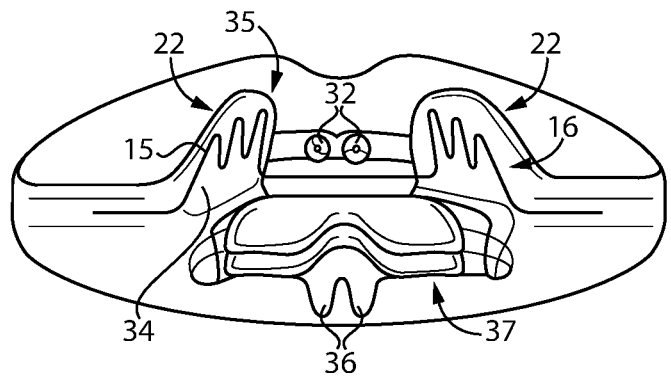
FIG. 4 is another rear view of a habit corrector appliance.

The positions of the first and second ramps 40 and 42 are also illustrated in FIGS. 2 and 4. The upper ramp 40 is very high almost within the palate to make sure the tongue learns to position itself in the palate which widens the palate and also prevents mouth breathing since the inferior part of the tongue (lower portion) prevents day and night mouth breathing. The lower ramp substantially prevents the tongue from entering the lower portion of the space within the oral cavity. The upper ramp 40 aids in the elevated tongue position and the patient learns to swallow with the tongue elevated. This position also substantially prevents any air to enter the oral cavity resulting from mouth breathing.

Figure 8:
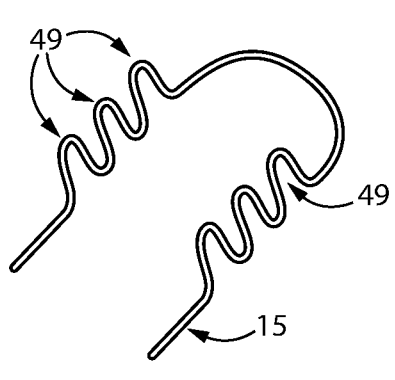
FIG. 8 is a perspective view of one embodiment of a wire embedded into a habit corrector appliance.

Slits 47 and 48 are located on the sides of both ramps 40 and 42 of FIG. 1 to allow unrestricted expansion or contraction of the posterior sections 28 and 30. An imbedded wire 15 (see FIGS. 4 and 8), that has vertically oriented wave structures 49, is located within the material forming the appliance 10. The wave structures 49 extend vertically from a relatively straight base line and include peaks that are generally rounded. The body at the upper arch is adjusted by moving the sections 28 and 30 of FIGS. 1 and 3 toward or away from each other. By spacing the sections 28 and 30 further apart from each other, the bodily widening of the upper arch is increased. In other embodiments, the wave structure includes peaks that are generally rectangular and periodic, such as a square wave. Other embodiments are contemplated including a wire the extends longitudinally along the inner shield 16 as well as extending vertically along the inner shield 16. In another embodiment, a wire, like the wire 15, is located at an inner shield located at the lower trough 30.

Figure 7:
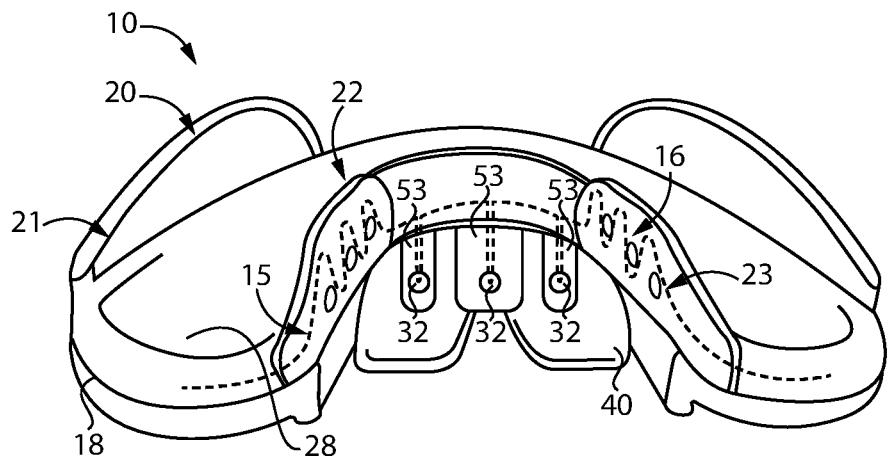
FIG. 7 is another embodiment of a rear view of a habit corrector appliance.
Figure 9:
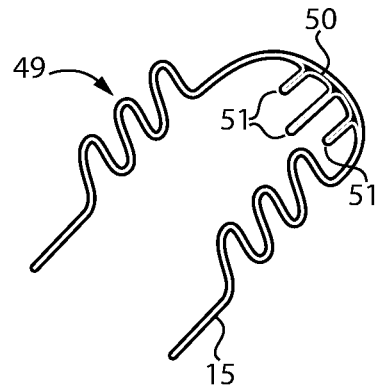
FIG. 9 is a perspective view of another embodiment of a wire embedded into a habit corrector appliance.
Figure 10:
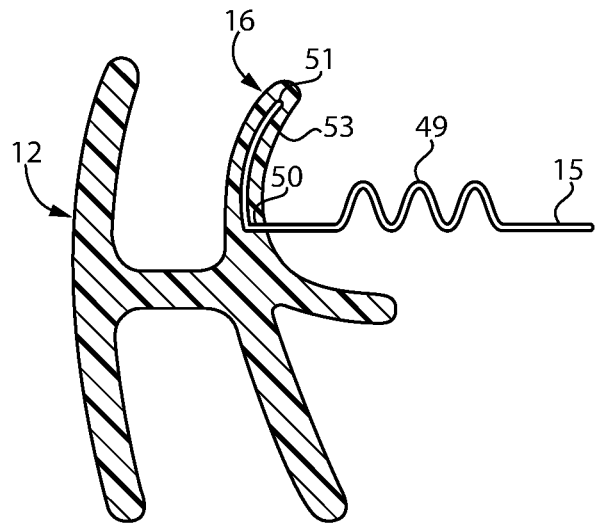
FIG. 10 is a side cross sectional view taken along a longitudinal centerline of another embodiment of the habit corrector appliance of FIG. 7.

An additional smaller diameter wire 50, i.e. 0.020 inch diameter, is attached to the main imbedded wire 15 in some embodiments as seen in FIG. 7 and FIG. 9. Other sizes of wires are contemplated. The wire 50 includes vertical undulations 51 that may have, for example 3 extension wires bent upward to fit within the palate. The wire 50 and the vertical undulations are imbedded into plastic tabs 53 (see FIG. 7), each of which extends upwardly from the lingual of the appliance when bent forward by hand toward the back of the upper teeth. Once the tabs 53 have been moved to locations at the back of the teeth the maxilla and incisor teeth are moved forward over a period of time. See FIGS. 7 and 8, The wire embedded tabs are used in appliances that allow the maxilla and upper incisors to be easily moved forward without any interference from a labial shield. FIG. 10 illustrates the wire 15 including the undulations 51 of wire 50 located within the inner shield 16. In a true sectional view, the wire 15 with undulations 49 would not be illustrated. In this view of FIG. 10, however, the oriented wave structures 49 and wire 15 are shown to illustrate an approximate location with respect to the shield 16.

The buccal posterior margins are also increased to more securely hold the appliance in place and to prevent jaw opening. The buccal posterior margin on the upper shield 35 is indicated by edge 21 of FIG. 1 and in the lower shield by edge 37 of FIG. 3.

Figure 5:
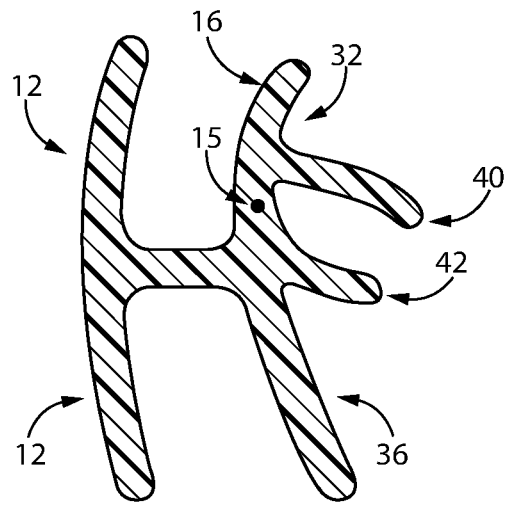
FIG. 5 is a side cross sectional view taken along a longitudinal centerline of the habit corrector appliance.

FIG. 5 is a side cross sectional view taken along a longitudinal centerline of the habit corrector appliance. As seen in FIG. 5, the upper ramp or shelf 40 and lower ramp or shelf 42 are spaced apart to maintain the position of the tongue. The upper, larger, longer first ramp 40 elevates the tongue and the lower, smaller, and shorter second ramp 42 substantially prevents and discourages the tongue from positioning itself into the lower jaw. The lingual tabs 36 are located below the lower shelf 42. Shelf 40 guides the tongue upward into the palate, while shelf 42 is shorter and prevents the tongue from finding a resting position withing the mandible body. The tongue rests on top of shelf 40 which prevents the patient from breathing through the mouth. Shelf 40 also can be curved slightly downward in the middle of the shelf to be more comfortable for the tongue. The lingual tabs 36 extend downward, are longer and more efficient which prevents the mandible from slipping posteriorly while sleeping, and it also keeps the mandible away from the orophaynx which prevents it from collapsing.

Additional embodiments are described as follows. While the embodiments, generally described a method for making appliances, the resulting device having the described features are also contemplated.

As disclosed herein, one embodiment of a habit corrector appliance includes forming a first trough and a second trough wherein each are lined with a material to reduce the likelihood of jaws opening to thereby reduce of prevent mouth breathing.

In another embodiment, there is provided a method of providing a corrector appliance having a wire that includes an imbedded undulating wire structure, such as vertical curves, wherein the undulating wire structure is molded into the lingual portion of the habit corrector appliance. The wire structure extends from one side of application, near a back left side for instance, to the other side of the appliance, near a back right side for instance In a further embodiment, there is provided a method of providing a corrector appliance having a wire that includes an imbedded undulating wire structure wherein the imbedded wires structure that are bendable while the wire holds its shape once bent to a desired location. The bendable wire enables a user to alter the shape of the appliance to widen or narrow distance between sides to modify the upper arch width.

In the same embodiment or other embodiments, there is provided a habit corrector appliance having a bendable wire that enables a user to alter the shape of the appliance to widen or narrow distance between sides is embedded into the lower arch of the appliance to modify the lower arch width.

In another embodiment, there is provided a method of preparing a habit corrector appliance with an upper shelf, a lower shelf, or both an upper and a lower shelf, wherein the shelves are not directly connected to the sides of appliance, but are separate from the sides to facilitate expanding or reducing the lateral distance between the sides. Once the distance has been set by a user, the imbedded wire holds its shape in the new selected position until a further manipulation of the wire.

In a further embodiment of a habit corrector appliance, a method includes preparing a habit corrector appliance wherein the upper and lower walls of the front of the appliance are exceptionally high to prevent mouth breathing even when the mouth is open and to stimulate nasal breathing. For instance, in one or more embodiments, "exceptionally high" is considered to be about a 25% increase from the values shown in Table 2 above. An illustration of such dimensions is shown in the following Table 3, where each of the dimensions is in millimeters. The columns indicate in Table #3 as A and B, FIG. 6 describe the recommended amounts of the height 20 of FIGS. 1 and 41 of FIG. 2 and what increases of 25% would be in Columns marked A (+25%) and B (+25%). A and B heights of 20 and 41 are found in the following Table 3.

| Age | A (FIG. 6) | A (+25%) | B (FIG. 6) | B (+25%) |
| --- | --- | --- | --- | --- |
| 2-4 yrs | 11.5 | 14.0 | 11.5 | 14.0 |
| 4-6 yrs | 13.0 | 16.0 | 13.0 | 16.0 |
| 6-12 yrs | 20.0 | 25.0 | 14.0 | 18.0 |
| Adult | 25.0 | 31.0 | 17.0 | 21.0 |

In another embodiment, there is provided a method of imbedding an appliance with a bendable wire, wherein the appliances are habit corrector appliances, Max A appliances, and Class III appliances. The Max A is an appliance that advances the upper incisors and the maxilla in an anterior (forward) position relative to the mandible (lower jaw). It does this by the three extended tabs attached to the upper lingual anterior shield. The tongue pressure against these tabs pushes the upper arch (teeth and bone) forward since there is no labial shield in this Max A (or Class III appliance).

The Class III appliance has the same upper as in the Max A but has a bumper on the lower anterior portion of the lower shield that exerts pressure rearward against the lower dentition. The Max A corrects midface retrusion and the Class III appliance corrects a mandibular prognathism (forward lower jaw) combined with treatment of the Maxillary retrusion.

Other embodiments include a method of making an appliance with an imbedded wire that includes additional wires attached to a main wire with various configuration that address other purposes such as advancing the maxilla and the upper teeth. The additional wire attached to the main wire is thinner, the same size as, or thicker than the main wire in some embodiments. In other embodiments, the features of the additional wire are included in a single main wire that includes a varying thickness or diameter.

In a further embodiment, there is method for making an appliance that includes an imbedded wire with curves in the posterior part of the base wire with additional wires of smaller diameter having several elevated extensions to place pressure on the maxilla and the maxillary anterior teeth to advance the maxilla and upper front teeth by pushing these wire extensions forward when embedded in the appliance.

One or more sleep questionnaires are used, depending on the age of the patient, to determine or to diagnose sleep disordered breathing. The most frequently used sleep questionnaire is for the age of 5-7 years of age that can also be used for individuals of 8-12 years of age. Each of the questionnaires provides a list of symptoms in the form of questions. The answers to the questions are used to determine whether a habit corrector appliance is recommended for a patient. In one embodiment, the determination is made an initial or first time before a patient begins use of the habit corrector appliances and again at a later or second time after a period of use, such as 6 months, to determine the effectiveness of the appliance and even further at later times to determine the permanence of the improvement or relapse which may occur several months and years later.

Figure 11:
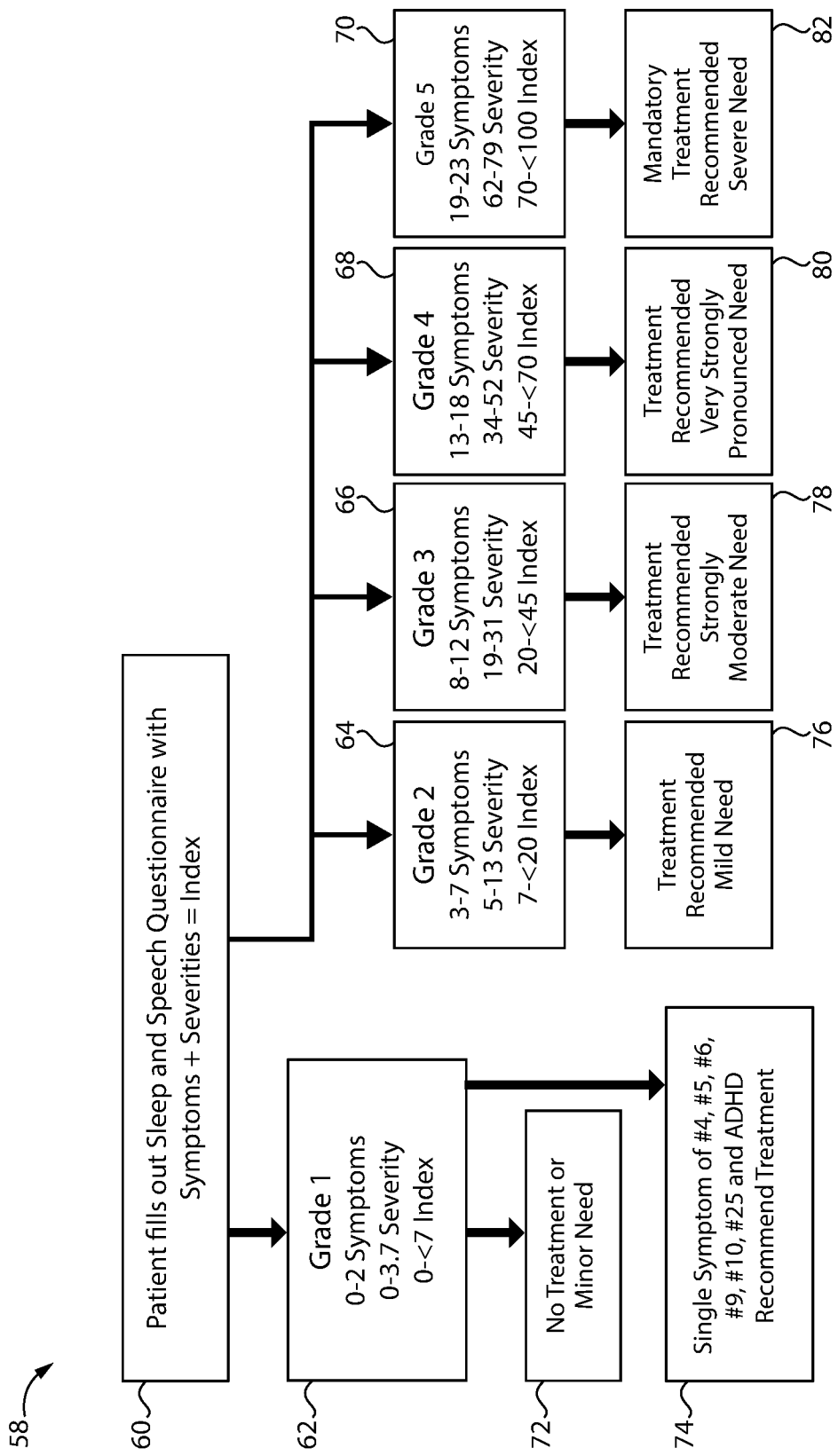
FIG. 11 illustrates a process chart for determining symptoms, severities, and indexes of sleep disordered breathing in determining treatment recommendations.

FIG. 11 illustrates one embodiment of an example of a flow chart 58 to determine or diagnose sleep disordered breathing which is used either alone or in combination with sleep questionnaires. If a sleep questionnaire is not used a practitioner may make a determination. If using a questionnaire, initially at block 60, a patient fills out a sleep and speech questionnaire (illustrated in FIG. 12) that includes a number of questions requiring answers, which when answered provide treatment recommendations. These questions cover one or more of the following symptoms: snoring; lisps; labored breathing; omits consonants; interrupted snoring; nasal speech or hoarseness; hyperactive; wets the bed; mouth breathing; often interrupts; headaches in the morning (A.M.); frequent infections; allergies; grinds teeth; excessive sweating; restless sleep; talks or walks in sleep; attention deficit; poor ability in school and wakes up at night. While each of these symptoms are present in one or more of the age-related questionnaires, other symptoms can be included as needed. In one or more embodiments, each of the symptoms is also characterized based on the severity of the symptom. For instance, in different embodiments, the severity is rated based on a scale of 0 to 5. Other scales are contemplated. A severity of 0 represents not present, 1-2 (about 1-2 times per week) is a mild severity. #3 is moderate severity (occurring about 3-4 times per week) and 4-5 is pronounced severity (almost always present in 5-7 nights per week).

Once the questionnaire is completed, the questionnaire is reviewed to determine the number of symptoms, the severity of the symptoms, and an index. The index is a value determined by adding the number of symptoms and a cumulative total severity. The cumulative total severity is determined by adding the severity value identified for each of the symptoms. See block 60. Once the index is determined, different treatment recommendations are made based on the results of the questionnaire. In this embodiment, there are levels of treatment identified as grade 1 at block 62, grade 2 at block 64, grade 3 at block 66, grade 4 at block 68, and grade 5 at block 70. Fewer or additional grades are contemplated. As seen in each of blocks, a treatment is recommended based on the severity. Each of the blocks also states the values of symptoms, the severity, and the index which are required to provide the recommended treatment and the need for treatment.

For instance, as seen in grade 1, block 62, no treatment is required or a minor need for treatment exists at block 72. Additionally, single symptoms of a certain type, such as types 4, 5, 6, 9, 10, 25 and ADHD recommend treatment at block 74.

Each of the blocks 64, 66, 68, and 70 include a recommended treatment and need for treatment as shown in corresponding blocks 76, 78, 80, and 82. As can be seen in FIG. 11, blocks 76, 78, 80 and 82 recommend treatment with a sleep habit corrector, but each has a different need ranging from a mild need in block 76, to a very strongly pronounced need in block 80. For grade 5, at block 70, mandatory treatment is recommended, and the need is considered to be severe. Once treatment is recommended, the recommended type of treatment is provided to the patient by the practitioner or artificial intelligence by computer directly to patient. The treatment includes in different embodiments, the number of treatment sessions in a day and the amount of time the appliance is located in place for each treatment session. The treatment can include suggested treatments which are strictly followed, suggested treatments that are adjusted by the practitioner, or computer or treatments that are designed by the practitioner or computer based on the results of an individual's completed survey.

While exemplary embodiments incorporating the principles of the present disclosure have been described herein, the present disclosure is not limited to such embodiments. Instead, this application is intended to cover any variations, uses, or adaptations of the disclosure using its general principles. Further, this application is intended to cover such departures from the present disclosure as come within known or customary practice in the art to which this disclosure pertains.

What is claimed is:

1. A habit corrector appliance comprising:
a first ramp including a top, a bottom, and a first terminating edge extending toward a rear of the appliance, the first ramp extending from a front portion of the appliance, the first ramp being an upper ramp located at a high position, wherein the upper ramp is adapted to elevate and guide a tongue of a user upward toward an elevated tongue position on the top of the upper ramp adjacent to or at a palate of the user and to direct the user's tongue to be positioned at a higher location next to the palate which as a result widens the palate and which also prevents or reduces mouth breathing, since the higher location of an inferior part of the tongue prevents day or night mouth breathing; and a second ramp having a top and a second terminating edge extending toward the rear of the appliance, wherein the first and second terminating edges have the same profile in the transverse plane, wherein the first terminating edge is not directly connected to the second terminating edge and the first terminating edge extends further toward the rear of the appliance than the second terminating edge, such that the second ramp is smaller and shorter than the first ramp, the second ramp extending from the front portion of the appliance, the second ramp being a lower ramp located at a position lower than and beneath the first ramp and defining a first space between the first terminating edge at the bottom of the first ramp and the second terminating edge at the top of the second ramp wherein the first space is adapted to prevent the tongue from being positioned anywhere below the first ramp, the second ramp is adapted to prevent the tongue from entering a lower portion of an oral cavity space within the oral cavity and to prevent the tongue from assuming a resting posture within the mandibular body, wherein when the appliance is worn, the first ramp aids in the elevated tongue position and the user learns to swallow with the tongue elevated to reduce or prevent air from entering the oral cavity through the mouth, wherein the front portion includes an outer shield, and an inner shield spaced from the outer shield, wherein the first ramp and the second ramp extend from the inner shield.

2. The habit corrector appliance of claim 1 wherein the outer shield defines a first trough with the inner shield, the first trough configured to receive teeth of an upper jaw of the user, and defines a second trough with the inner shield, the second trough configured to receive teeth of a lower jaw of the user.

3. The habit corrector appliance of claim 2 wherein the first trough and the second trough are lined with a material to reduce a likelihood of jaws opening to thereby reduce or prevent mouth breathing.

4. The habit corrector appliance of claim 3 wherein the first trough and the second trough are configured for relining of each of the first trough and the second trough with a resin material to prevent mouth breathing from occurring and becoming a habit.

5. The habit corrector appliance of claim 4 wherein the inner shield includes a wall extending generally upwardly from the first trough, the wall including a first side facing the first trough and a second side facing a second space of the habit corrector configured to receive the tongue, wherein one or more posterior bumps are located on the wall of the inner shield to remind the user of proper position of the tongue when swallowing.

6. The habit corrector appliance of claim 5 further comprising one or more lingual tabs, wherein the one or more the lingual tabs extend from the front portion toward the rear of the appliance to encourage the mandible to be positioned anteriorly and to prevent the mandible from slipping rearward during sleep to increase treatment success of mouth breathing, mandibular advancement and keeping the oropharynx to be open by resisting its closure by the mandible and tongue from drifting posteriorly.

7. The habit corrector appliance of claim 4 wherein at least one of the first trough, the second trough, and the shields are texturized to assist in retention of the resin material.

8. The habit corrector appliance of claim 2 further comprising one or more slits located at lateral edges of both of the first ramp and second ramp to provide for expansion of both of the first trough and the second trough, where in the lateral edges of the first ramp are not directly connected to the lateral edges of the second ramp.

9. The habit corrector applicant of claim 1 wherein the first ramp is curved downward toward the rear of the appliance.

* * * * *